US00PP37305P3

(12) United States Plant Patent
Wilde

(10) Patent No.: US PP37,305 P3
(45) Date of Patent: Mar. 3, 2026

(54) ***DAHLIA* PLANT NAMED 'KLEDH22563'**

(50) Latin Name: ***Dahlia* sp.**
Varietal Denomination: KLEDH22563

(71) Applicant: KLEMM + SOHN GMBH & CO. KG, Stuttgart (DE)

(72) Inventor: Katinka Wilde, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/774,918

(22) Filed: Jul. 16, 2024

(65) Prior Publication Data

US 2026/0026417 P1 Jan. 22, 2026

(51) Int. Cl.
*A01H 5/02* (2018.01)

(52) U.S. Cl.
USPC ..... Plt./321

(58) Field of Classification Search
USPC ..... Plt./321
CPC . A01H 5/02; A01H 5/00; A01H 6/144; A01H 6/14
See application file for complete search history.

(56) References Cited

PUBLICATIONS

Ball Seed City Lights Apricot Glow Dahlia, retrieved on Jul. 3, 2025 at https://www.ballseed.com/PlantInfo/?phid=021708422000298, one page. (Year: 2025).*
Ball Seed Dalaya Apricot+Red Eye Dahlia, retrieved on Jul. 7, 2025 at https://www.ballseed.com/PlantInfo/?phid=021706572000302, one page. (Year: 2025).*
Facebook Selecta One 2023 Selecta one's post, retrieved on Jul. 3, 2025 at https://www.facebook.com/selectaone1/posts/one-of-our-new-highlights-for-the-coming-season-is-dahlia-meena-ajala-it-has-got/710285804434338/, one page. (Year: 2023).*
Selecta One Spring Annuals Trixi 2023/2024, retrieved on Jul. 3, 2025 at https://daigelis.lt/wp-content/uploads/2021/08/Spring-Selecta.pdf, cover page, one introductory page, pp. 1-3, 18-19, 156-157 (5 p. total). (Year: 2024).*
UT Gardens Jackson Lunchtime Liquidation Sale, retrieved on Jul. 3, 2025 at https://westtn.tennessee.edu/wp-content/uploads/sites/35/2024/05/Liquidation-Spring-Plant-sale-2024-for-distribution-2.pdf, 13 pp. (Year: 2024).*

* cited by examiner

*Primary Examiner* — June Hwu
(74) *Attorney, Agent, or Firm* — Weatherly IP Solutions, LLC; Karen P. Bechtold; James M. Weatherly

(57) ABSTRACT

A new *Dahlia* plant designated 'KLEDH22563' particularly distinguished by daisy-eyed double orange flowers with a darker, reddish-orange at the center of the flowers, medium flower size, and dark green leaves, is disclosed.

1 Drawing Sheet

Genus and species: *Dahlia* sp.
Variety denomination: 'KLEDH22563'.

BACKGROUND

The present invention comprises a new and distinct variety of *Dahlia*, botanically known as *Dahlia* sp., and hereinafter referred to by the variety name 'KLEDH22563'. 'KLEDH22563' originated from an open pollination in a field with the female proprietary *Dahlia* DH-2016-3224 (unpatented) and an unknown male *Dahlia* plant in May 2016 in Stuttgart, Germany. In May 2016 a seedling was selected and named 'KLEDH22563'. 'KLEDH22563' was first vegetatively propagated by vegetative cuttings in May 2017 in Stuttgart, Germany. 'KLEDH22563' was found to reproduce true to type in successive generations of asexual propagation.

SUMMARY

The following are the most outstanding and distinguishing characteristics of 'KLEDH22563' when grown under normal horticultural practices in Stuttgart, Germany.

1. Daisy-eyed double orange flowers with darker, reddish-orange center;
2. Medium flower size; and 3. Dark green leaves.

DESCRIPTION OF THE PHOTOGRAPH

This new *Dahlia* plant is illustrated by the accompanying photograph of the plant approximately fifteen weeks old and grown in a greenhouse in Stuttgart, Germany. The photograph shows the whole plant, unless otherwise noted, including the inflorescences and foliage and buds and was taken in January 2023 in Stuttgart, Germany. The colors shown are as true as can be reasonably obtained by conventional photographic procedures.

DESCRIPTION OF 'KLEDH22563'

The following detailed descriptions set forth the distinctive characteristics of 'KLEDH22563'. The data which define these characteristics were collected from asexual reproductions carried out in Stuttgart, Germany. Data was collected in April 2024 on 16-week-old plants potted at week four and grown in a plastic greenhouse. Color references are to The R.H.S. Colour Chart of The Royal Horticultural Society of London (R.H.S.), 5$^{th}$ edition (2007).

Classification:
*Family*.—Asteraceae.
*Botanical*.—*Dahlia* sp.
*Designation*.—'KLEDH22563'.
Parentage:
*Female parent*.—'DH-2016-3224' (unpatented).
*Male parent*.—Unknown male parent.
Propagation:
*Type*.—Vegetative terminal cuttings.
*Time to produce a rooted young plant*.—3 weeks.
*Root description*.—RHS N155C in color, fine.
*Rooting habit*.—Freely branching and moderately dense.
Plant description:
*Plant and growth habit*.—Plant and growth habit: upright, free basal branching, and inflorescences held above the foliar plane.
*Plant height*.—28.0 cm.
*Plant diameter*.—30.0 cm.
Lateral branches:
*Length*.—14.0 cm.
*Diameter*.—0.4 cm.
*Internode length*.—4.0 cm.
*Aspect*.—Outwardly spreading.
*Strength*.—Medium strong.
*Texture*.—Smooth.
*Color*.—RHS 137C.
Foliage description:
*Arrangement*.—Predominantly pinnate with 5 leaflets.
*Leaf wing*.—Absent to weak.
*Length*.—10.5 cm.
*Width*.—10.0 cm.
*Shape*.—Oval.
*Apex*.—Acute.
*Base*.—Acute.
*Margin*.—Moderately serrate.
*Venation pattern*.—Pinnate.
*Venation color*.—RHS N137A.
*Texture*.—Upper surface: Smooth. Lower surface: Smooth.
*Color*.—Immature: Upper surface: RHS 137A. Lower surface: RHS 137C. Mature: Upper surface: RHS N137A. Lower surface: RHS 138B.
Petioles:
*Length*.—3.5 cm.
*Diameter*.—0.4 cm.
*Texture*.—Upper surface: Smooth. Lower surface: Smooth.
*Color*.—Upper surface: RHS 148A. Lower surface: RHS 148A.
Inflorescence description:
*Appearance and arrangement*.—Attitude is semi-upright, flower head arranged moderately above the foliage.
*Fragrance*.—Absent.
*Time to flower*.—In the winter, about 3 months after planting; in the summer, about 2 months after planting.
*Post-production longevity*.—Plants flower continuously from spring through autumn.
Inflorescence bud:
*Height*.—1.5 cm.
*Diameter*.—1.5 cm.
*Shape*.—Oblate.
*Color*.—RHS 150A.
Inflorescence size and color:
*Diameter*.—8.0 cm.
*Depth* (*height*).—4.0 cm.
*Disc diameter*.—2.0 cm.
*Receptacle height*.—1.0 cm.
*Receptacle diameter*.—2.0 cm.
*Receptacle color*.—RHS 151A and gradually turning to RHS N137A at the base.
Ray florets:
*Quantity per inflorescence*.—Approximately 50.
*Length*.—4.0 cm.
*Width*.—2.0 cm.
*Shape*.—Elliptic.
*Apex*.—Obtuse.
*Base*.—Moderately involute, Rounded.
*Margin*.—Entire.
*Aspect*.—Semi-upright.
*Profile in cross-section at mid-point*.—Moderately concave.
*Longitudinal axis shape*.—Straight.
*Texture*.—Upper surface: Smooth. Lower surface: Smooth.
*Color*.—Immature: Upper surface: Basis RHS 42A as a color gradient to RHS N30A. Lower surface: RHS 24B. Mature: Upper surface: RHS 14A at the tip, RHS 42A at the base and RHS N30A in the middle. Lower surface: RHS 14C.
Disc florets:
*Quantity per inflorescence*.—Approximately 25.
*Length*.—1.5 cm.
*Diameter*.—0.2 cm.
*Shape*.—Elliptic.
*Texture*.—Inner surface: Smooth. Outer surface: Smooth.
*Color*.—Immature: Inner surface: RHS 35A. Outer surface: RHS 35B. Mature: Inner surface: RHS N34C. Outer surface: RHS N34A.
Phyllaries:
*Quantity per inflorescence*.—8.
*Length*.—1.8 cm.
*Width*.—0.6 cm.
*Shape*.—Elliptic.
*Apex*.—Acute.
*Base*.—Acute.
*Margin*.—Entire.
*Texture*.—Upper surface: Smooth. Lower surface: Smooth.
*Color*.—Upper surface: RHS 151C on basis RHS 144B. Lower surface: RHS 151C on basis RHS 144B.
Peduncles:
*Length, terminal peduncle*.—20.0 cm.
*Length, axillary peduncle*.—6.0 cm.
*Diameter*.—0.3 cm.
*Aspect*.—Semi-upright.
*Strength*.—Strong.
*Texture*.—Smooth.
*Color*.—RHS 148A.
Reproductive organs:
*Androecium*.—Present on disc florets only. Quantity per floret: 4. Filament length: 0.4 cm. Filament color: RHS 155D. Anther shape: Long lanceolate. Anther length: 0.5 cm. Anther color: RHS N167A. Pollen amount: Abundant. Pollen color: RHS 23A.

*Gynoecium*.—Present on disc florets and on innermost row of ray florets. Quantity per floret: 1. Pistil length: 1.0 cm. Style length: 0.5 cm. Style color: RHS 13D. Stigma shape: Lanceolate pinnate. Stigma color: RHS 13A. Ovary color: RHS 8D.

Fruit and seed set: Not yet observed.

Disease and pest/insect resistance: No disease resistance observed.

COMPARISON OF 'KLEDH22563' WITH PARENTAL LINE AND KNOWN VARIETY

'KLEDH22563' is distinguished from the parent as described in Table 1.

TABLE 1

Comparison with Parental Line

| Trait | Variety 'KLEDH22563' | Female parent DH-2016-3224 |
|---|---|---|
| Flower size | Medium | Small |
| Foliage | Medium dark leaves | Really dark leaves |

'KLEDH22563' can be compared to the commercial *Dahlia* variety 'KLEDH22140' (unpatented). Differences between the varieties are described in Table 2.

TABLE 2

Comparison with Similar Variety

| Trait | Variety 'KLEDH22563' | Commercial line KLEDH22140 |
|---|---|---|
| Filling | Daisy-eyed double | Single to semi-double |
| Foliage colour | Dark green | Green |
| Ray floret color | Orange florets that gradually becomes a darker reddish-orange at the base | Orange florets with red coloration at the base |

I claim:

1. A new and distinct variety of *Dahlia* plant designated 'KLEDH22563', as illustrated and described herein.

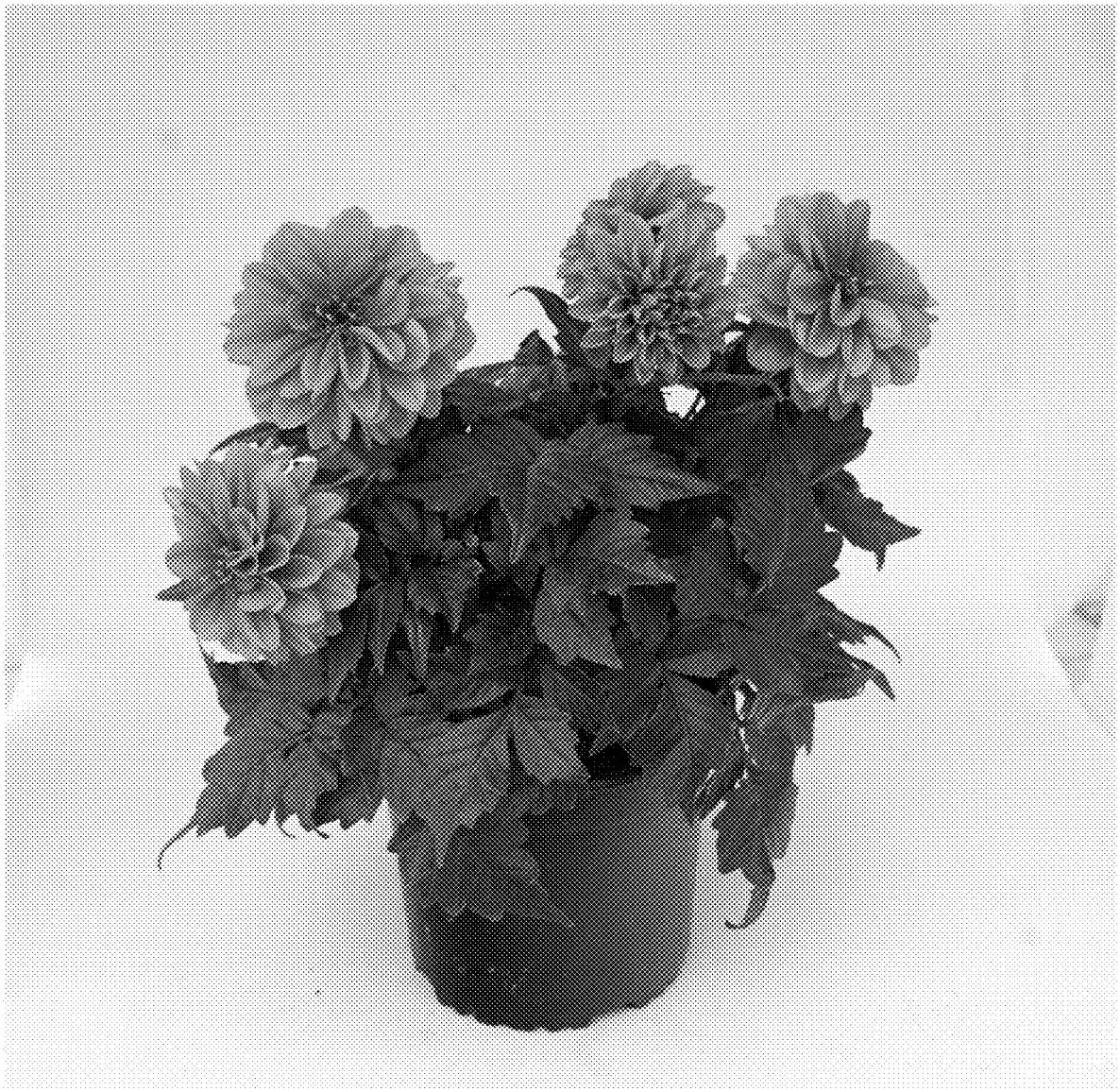

* * * * *